(12) United States Patent
Fujimoto et al.

(10) Patent No.: US 8,631,713 B2
(45) Date of Patent: Jan. 21, 2014

(54) DEVICE FOR MEASURING COMPRESSIVE FORCE OF FLEXIBLE LINEAR BODY

(75) Inventors: Hideo Fujimoto, Nagoya (JP); Akihito Sano, Nagoya (JP); Yoshitaka Nagano, Iwata (JP)

(73) Assignees: National University Corporation Nagoya Institute of Technology, Aichi (JP); NTN Corporation, Osaka (JP)

(*) Notice: Subject to any disclaimer, the term of this patent is extended or adjusted under 35 U.S.C. 154(b) by 777 days.

(21) Appl. No.: 12/439,793

(22) PCT Filed: Aug. 30, 2007

(86) PCT No.: PCT/JP2007/066893
§ 371 (c)(1),
(2), (4) Date: Mar. 3, 2009

(87) PCT Pub. No.: WO2008/029705
PCT Pub. Date: Mar. 13, 2008

(65) Prior Publication Data
US 2010/0030115 A1 Feb. 4, 2010

(30) Foreign Application Priority Data
Sep. 5, 2006 (JP) .................................. 2006-240607

(51) Int. Cl.
*G01L 1/24* (2006.01)
(52) U.S. Cl.
USPC ...................................... 73/862.624; 600/587
(58) Field of Classification Search
USPC ......... 600/433, 434, 435, 466, 585, 587, 547, 600/505; 73/1.15, 862.581, 862.624; 374/199
See application file for complete search history.

(56) References Cited

U.S. PATENT DOCUMENTS

| | | | | |
|---|---|---|---|---|
| 4,773,865 A | * | 9/1988 | Baldwin | ........................ 434/268 |
| 5,064,121 A | * | 11/1991 | Bolduc | .......................... 239/309 |

(Continued)

FOREIGN PATENT DOCUMENTS

| | | |
|---|---|---|
| JP | 59-47241 | 11/1984 |
| JP | 10-263089 | 10/1998 |

(Continued)

OTHER PUBLICATIONS

European Search Report issued in European Patent Application No. 07806370.8-1236, dated Feb. 1, 2011.

*Primary Examiner* — Max Hindenburg
*Assistant Examiner* — Renee Danega
(74) *Attorney, Agent, or Firm* — McDermott Will & Emery LLP

(57) ABSTRACT

A measurement device capable of sensing presence of an obstacle within a vessel from outside the vessel in operating a linear body inserted in the vessel is provided. According to this measurement device, an easy-to-use measurement device capable of measuring compressive force in a direction of longitudinal axis applied to the linear body that has a sheath thicker than the linear body, such as a wire having a coil for embolizing an aneurysm attached at a tip end, without lowering measurement accuracy, can be provided. In addition, a length of a restraint portion is minimized, to achieve a smaller size of the measurement device. Moreover, the measurement device capable of measuring compressive force in the direction of longitudinal axis applied to the linear body regardless of magnitude of buckling load of the linear body can be provided, and the same measurement device is applicable to linear bodies of various materials, which leads to cost efficiency.

10 Claims, 6 Drawing Sheets

(56) References Cited

U.S. PATENT DOCUMENTS

| | | | |
|---|---|---|---|
| 5,386,720 A * | 2/1995 | Toda et al. | 73/105 |
| 5,791,350 A * | 8/1998 | Morton | 600/590 |
| 5,810,717 A * | 9/1998 | Maeda et al. | 600/151 |
| 6,272,371 B1 | 8/2001 | Shlomo | |
| 6,344,086 B1 * | 2/2002 | Okada et al. | 118/125 |
| 6,361,606 B1 * | 3/2002 | Jairazbhoy | 118/410 |
| 6,570,107 B1 * | 5/2003 | Nishimoto et al. | 200/6 R |
| 6,591,143 B1 * | 7/2003 | Ekwall | 607/116 |
| 6,981,945 B1 | 1/2006 | Sarvazyan et al. | |
| 7,156,832 B2 * | 1/2007 | Drevik et al. | 604/385.31 |
| 7,478,009 B2 * | 1/2009 | Cabrera et al. | 600/587 |
| 2001/0007685 A1 * | 7/2001 | Kasuga et al. | 425/411 |
| 2001/0027727 A1 * | 10/2001 | Miyachi et al. | 100/219 |
| 2004/0059260 A1 * | 3/2004 | Truwit | 600/585 |
| 2005/0033285 A1 * | 2/2005 | Swanson et al. | 606/41 |
| 2005/0228274 A1 | 10/2005 | Boese et al. | |
| 2006/0195049 A1 * | 8/2006 | Whalen et al. | 600/587 |

FOREIGN PATENT DOCUMENTS

| | | |
|---|---|---|
| JP | 2001-215158 | 8/2001 |
| JP | 2002-029381 | 1/2002 |
| JP | 2006-064465 | 3/2006 |
| WO | WO 2007/111182 A1 | 10/2007 |

* cited by examiner

# DEVICE FOR MEASURING COMPRESSIVE FORCE OF FLEXIBLE LINEAR BODY

RELATED APPLICATIONS

This application is the U.S. National Phase under 35 U.S.C. §371 of International Application No. PCT/JP2007/066893, filed on Aug. 30, 2007, which in turn claims the benefit of Japanese Application No. 2006-240607, filed on Sep. 5, 2006, the disclosures of which Applications are incorporated by reference herein.

TECHNICAL FIELD

The present invention relates to a force measurement device and particularly to a device for measuring compressive force applied to a linear body having flexibility.

BACKGROUND ART

A linear body having flexibility has been put into practical use as a linear medical appliance inserted in a vessel in a body. For example, a guide wire or a catheter inserted in a vessel in a body such as a blood vessel, a ureter, a bronchus, an alimentary canal, or a lymph vessel, or a wire having an embolization coil attached at a tip end for embolizing an aneurysm has been known. Such a linear body is inserted into a vessel in a body and guided to a destination through an operation from outside the body.

In many cases, the vessel in which the linear body is inserted is not necessarily linear but partially flexed or branched. In addition, a diameter of the vessel is not necessarily uniform, and the vessel itself may become thinner or a diameter of the vessel may be made smaller by an obstacle located in the vessel such as a thrombus in a blood vessel. A conventional linear body, however, has not been provided with means for sensing a condition in a direction of travel of the linear body, and it has been necessary to use operator's intuition in operating the linear body and the operator has had to be skilled in the operation for guiding the linear body from outside the body. A device provided with a pressure sensor at a tip end of a linear body is disclosed in Japanese Patent Laying-Open No. 10-263089 (Patent Document 1) as a device sensing presence of an obstacle in a direction of travel of the linear body.

Patent Document 1: Japanese Patent Laying-Open No. 10-263089

DISCLOSURE OF THE INVENTION

Problems to be Solved by the Invention

On the other hand, it is difficult to realize a device provided with a pressure sensor at the tip end of a linear body, in particular when the linear body is extremely thin. For example, a guide wire to be inserted in a cerebral blood vessel has a diameter around 0.35 mm, and it is difficult to provide a small pressure sensor at the tip end of such an extremely thin linear body. In addition, it is more difficult to insert a wire in the linear body in order to extract a signal from the pressure sensor to the outside.

Moreover, if the vessel in which the linear body is inserted is flexed or if a diameter of the vessel is small, insertion resistance of the linear body is affected by friction with the vessel. Accordingly, an output from the pressure sensor provided at the tip end of the linear body may not necessarily be in agreement with kinesthetic sense of the operator at the time of insertion. Therefore, even when the device provided with the pressure sensor at the tip end of the linear body is used, the operator operates the linear body based on kinesthetic sense information of the insertion resistance of the linear body externally held with fingers of the operator, that is, relying on intuition of the operator. Further, as it is only the operator that can feel the kinesthetic sense, it is difficult to quantify manipulation of a skilled operator so as to transfer the skill to a less experienced operator.

In addition, it is not cost effective to prepare linear bodies of various materials for adaptation to different applications and to provide pressure sensors in respective linear bodies, and manufacturing cost is increased.

Therefore, a main object of the present invention is to provide a measurement device capable of sensing presence of an obstacle within a vessel from outside the vessel in operating the linear body inserted into the vessel, which is applicable to linear bodies of various materials.

Means for Solving the Problems

A measurement device according to the present invention is a measurement device measuring compressive force in a direction of longitudinal axis applied to a linear body having flexibility, and includes a main body in which a through hole through which the linear body passes is formed, the linear body being bent in a prescribed direction within the through hole when the compressive force in the direction of longitudinal axis is applied to the linear body. In addition, the measurement device includes a sensor detecting a degree of bending of the linear body. Moreover, the measurement device includes a conversion circuit converting the degree of bending of the linear body detected by the sensor into the compressive force in the direction of longitudinal axis applied to the linear body. In an inner wall of the through hole, a groove is formed to penetrate the main body along the through hole.

Here, a groove having a width and a depth greater than a diameter of the through hole is formed in the inner wall of the through hole. In a wire having a coil for embolizing an aneurysm attached to the tip end, the coil at the tip end is soft. Therefore, the coil is accommodated in a sheath and the sheath is thicker than the wire. Accordingly, by using the measurement device in which the groove allowing passage only of the sheath accommodating the coil is formed in inserting the wire having the coil for embolizing an aneurysm attached to the tip end into a blood vessel, compressive force in the direction of longitudinal axis applied to the wire can be measured. As movement of the wire in a direction other than the direction of longitudinal axis is restricted within the measurement device, measurement accuracy can be maintained and an easy-to-use measurement device without requiring insertion of the wire with the sheath being removed into the through hole of the measurement device can be provided.

Preferably, the groove is formed along the inner wall of the through hole located on an inner side of bending of the linear body within the through hole in which the linear body is bent. In addition, the through hole is formed such that the inner wall of the through hole located on an outer side of bending of the linear body is distant from the inner wall of the through hole located on the inner side of bending of the linear body by a distance exceeding the sum of a width of the groove and a diameter of the linear body to form a space within the through hole in which the linear body is bent.

Here, the groove is formed along the inner wall of the through hole located on the inner side of bending of the linear body, which is a location irrelevant to movement of the linear body involved with bending, when compressive force in the direction of longitudinal axis is applied to the linear body to bend the linear body in the space within the through hole in which the linear body is bent. Therefore, lowering in accuracy in measuring compressive force caused by interference of the groove with bending of the linear body can be prevented.

In addition, preferably, the through hole is formed to have restraint portions restricting movement of the linear body in a direction other than the direction of longitudinal axis, at opposing end portions thereof, and the through hole is formed such that the linear body is in parallel to the restraint portions outside a port of the main body through which the linear body passes, when the linear body passes through the through hole and no external force other than gravity is applied to the linear body. Here, a length of the restraint portion necessary for avoiding lowering in measurement accuracy is defined based on parallelism between the linear body and the restraint portion. Therefore, the length of the restraint portion is minimized so as to achieve a smaller size of the measurement device.

When the groove is formed in the inner wall of the through hole to penetrate the main body along the through hole, a dimension of a cross-section of the restraint portion perpendicular to a direction of extension thereof is identical to a dimension of a cross-section of the groove. Here, if a length of the restraint portion is insufficient, the linear body moves in a direction other than the direction of longitudinal axis in the restraint portion, which results in lowering in measurement accuracy. Therefore, by defining the length of the restraint portion based on parallelism between the linear body and the restraint portion also when the groove is formed, lowering in measurement accuracy can be prevented.

In addition, preferably, the through hole is formed such that an inner wall of the through hole located on an outer side of bending of the linear body is distant from the inner wall of the through hole located on an inner side of bending of the linear body to form a space within the through hole in which the linear body is bent. Moreover, the through hole is formed such that the inner wall of the through hole located on the outer side of bending of the linear body is in a shape of a curved surface convex toward the inside of the through hole. Here, when compressive force in the direction of longitudinal axis is applied to the linear body to bend the linear body in a space within the through hole in which the linear body is bent, the linear body is bent along the inner wall of the through hole located on the outer side of bending of the linear body. Therefore, buckling of the linear body within the space can be prevented. Accordingly, compressive force in the direction of longitudinal axis applied to the linear body can accurately be measured over a wide range.

In addition, preferably, the through hole is formed such that a part of the linear body is distant from the inner wall of the through hole located on the outer side of bending of the linear body when the compressive force in the direction of longitudinal axis is applied to the linear body to bend the linear body. Moreover, the through hole is formed such that a distance between contact points at which the linear body moves away from the inner wall is smaller as the compressive force increases. Here, compressive force in the direction of longitudinal axis applied to the linear body can accurately be measured without buckling of the linear body of which buckling load is small. Therefore, the measurement device capable of measuring compressive force in the direction of longitudinal axis applied to the linear body regardless of magnitude of buckling load of the linear body can be provided, and the same measurement device is applicable to linear bodies of various materials, which leads to cost efficiency.

In addition, preferably, the through hole is formed to have restraint portions restricting movement of the linear body in a direction other than the direction of longitudinal axis, at opposing end portions thereof, and the through hole is formed such that an angle between extensions of the restraint portions is not smaller than 30° and not greater than 50°. Here, by defining the angle between the extensions of the restraint portions, the linear body can readily pass through the measurement device when it is inserted in the measurement device.

In addition, preferably, the through hole is formed such that an angle between an extension of the restraint portion and a tangent to the inner wall on the extension, of the through hole located on the outer side of bending of the linear body is not smaller than 100° and not greater than 130°. Here, by defining the angle between the extension of the restraint portion and the tangent to the inner wall on the extension, of the through hole located on the outer side of bending of the linear body, the linear body can readily pass through the measurement device when it is inserted in the measurement device.

In addition, preferably, the measurement device above is incorporated in medical equipment for use. For example, when the measurement device is incorporated in a Y-connector for use, the linear body is operated through an input port of the Y-connector and a medicine can be injected through another input port.

In addition, preferably, the measurement device above is attached to a training simulator simulating a human body for use. Here, manipulation of a skilled operator can be quantified and manipulation can quantitatively be transferred to a less experienced operator. Therefore, manipulation of the less experienced operator can quickly be improved.

Effects of the Invention

As described above, according to this measurement device, an easy-to-use measurement device capable of measuring compressive force in the direction of longitudinal axis applied to the linear body that has a sheath thicker than the linear body, such as a wire having a coil for embolizing an aneurysm attached at a tip end, without lowering measurement accuracy, can be provided. In addition, a length of the restraint portion is minimized, to achieve a smaller size of the measurement device. Moreover, the measurement device capable of measuring compressive force in the direction of longitudinal axis applied to the linear body regardless of magnitude of buckling load of the linear body can be provided, and the same measurement device is applicable to linear bodies of various materials, which leads to cost efficiency.

Figure 1:
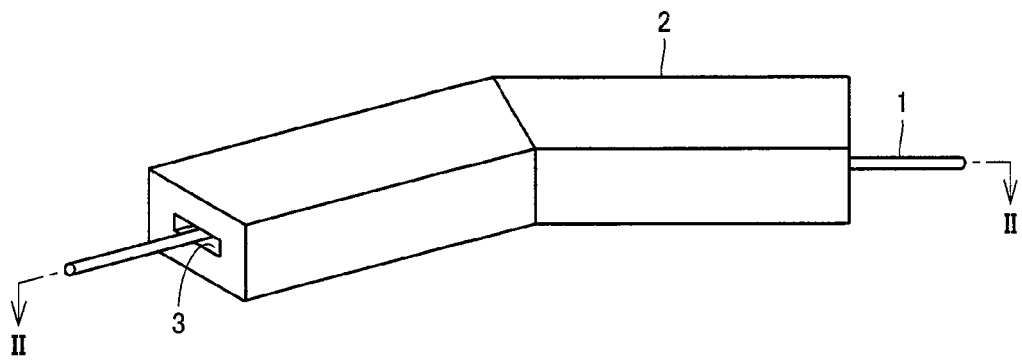
FIG. 1 is a schematic diagram showing appearance of a main body of a measurement device according to one embodiment of the present invention.

DESCRIPTION OF THE REFERENCE SIGNS 1, 1a, 1b linear body; 2 measurement device main body; 3 through hole; 4 input/output port; 5, 6 restraint portion; 7, 8, 9 inner wall; 10 recess; 11 space; 12 groove; 13 coil; 14, 14a, 14b delivery wire; 15 sheath; 16 line sensor; 17 lens; 18 Y-connector; 19 input port; 20 another input port; 21 output port; 22 visualizing instrument; 23 guide wire; 24 catheter; 25 operator; 26 simulator; 27 simulated perspective image; and 28 cable.

BEST MODES FOR CARRYING OUT THE INVENTION

An embodiment of the present invention will be described hereinafter with reference to the drawings. In the drawings below, the same or corresponding elements have the same reference characters allotted and detailed description thereof will not be repeated.

FIG. 1 is a schematic diagram showing appearance of a main body of a measurement device according to one embodiment of the present invention. In FIG. 1, this measurement device includes a measurement device main body 2, and in measurement device main body 2, a through hole 3 through which a linear body 1 having flexibility passes is formed.

Figure 2:
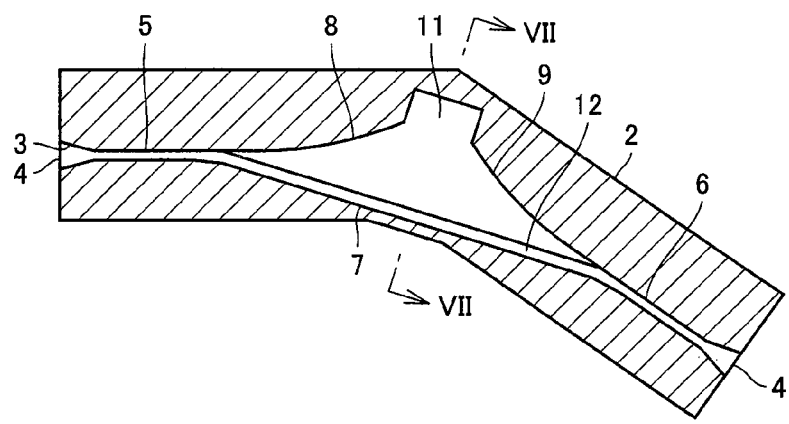
FIG. 2 is a cross-sectional schematic diagram showing an internal structure of the main body of the measurement device shown in FIG. 1.

FIG. 2 is a cross-sectional schematic diagram showing an internal structure of the main body of the measurement device along the line II-II shown in FIG. 1. In FIG. 2, at an inlet and an outlet of through hole 3, a tapered input/output port 4 is formed in order to facilitate insertion, by making greater the inlet and the outlet where linear body 1 passes. Through hole 3 is formed to have restraint portions 5, 6 restricting movement of linear body 1 in a direction other than the direction of longitudinal axis on opposing end portions thereof.

Measurement device main body 2 defines a direction of bending of linear body 1 within through hole 3 when compressive force in the direction of longitudinal axis is applied to linear body 1. Namely, through hole 3 is curved between restraint portions 5, 6 and linear body 1 is in a bent shape when it passes through through hole 3. In addition, through hole 3 is formed such that inner walls 8, 9 are distant from an inner wall 7 by a distance exceeding the sum of a width of a groove 12 which will be described later and a diameter of linear body 1 to form a space 11 within through hole 3. In space 11, an operation of linear body 1 in a direction in parallel to a sheet surface is not restrained. In space 11, a height of through hole 3 in a direction perpendicular to the sheet surface is slightly greater than the diameter of linear body 1 (for example, 105% to 120% of the diameter of linear body 1), so as to restrain the operation of linear body 1 in the direction perpendicular to the sheet surface. Namely, through hole 3 in a cross-section perpendicular to the direction of longitudinal axis of linear body 1 has a rectangular cross-section. Thus, a direction of bending of linear body 1 within through hole 3 is defined, and linear body 1 is positioned such that a height of peak of bending of linear body 1, that is, a distance from inner wall 7 to linear body 1, when compressive force in the direction of longitudinal axis is applied to linear body 1, is set.

Groove 12 is formed to penetrate measurement device main body 2 along inner wall 7 of through hole 3. Groove 12 is formed to have a diameter greater than the diameter of linear body 1, that is, to have a width and a depth greater than the diameter of linear body 1.

Figure 3:
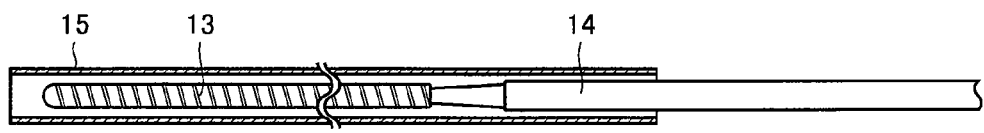
FIG. 3 is a schematic diagram showing a structure of a wire having a coil for embolizing an aneurysm attached at a tip end.

A structure of a wire for embolizing an aneurysm will be described by way of example of the linear body, with regard to which the measurement device shown in FIGS. 1 and 2 is capable of measuring compressive force in the direction of longitudinal axis. FIG. 3 is a schematic diagram showing the structure of the wire having a coil for embolizing an aneurysm attached at a tip end. In FIG. 3, the wire for embolizing an aneurysm with coil is divided into a coil 13 for embolizing an aneurysm and a delivery wire 14 (here, delivery wire 14 corresponds to linear body 1) held by hand in inserting the wire into a blood vessel. As coil 13 at the tip end serves to embolize an aneurysm, it is very soft and manufactured such that it is wound around a prescribed diameter when it is not restrained. Therefore, before use, the coil is accommodated in a sheath 15 and restrained not to be wound. Sheath 15 has a diameter greater than that of delivery wire 14.

Figure 4:
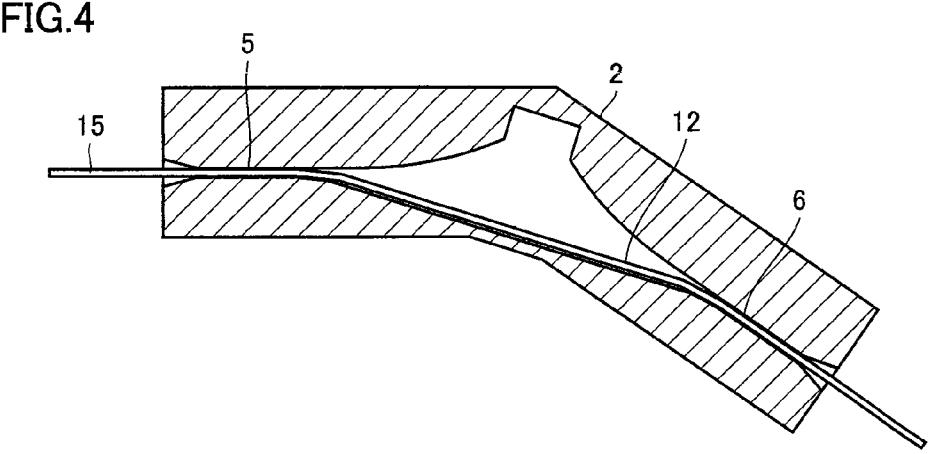
FIG. 4 is a cross-sectional schematic diagram showing such a state that a sheath passes through the measurement device.
Figure 5:
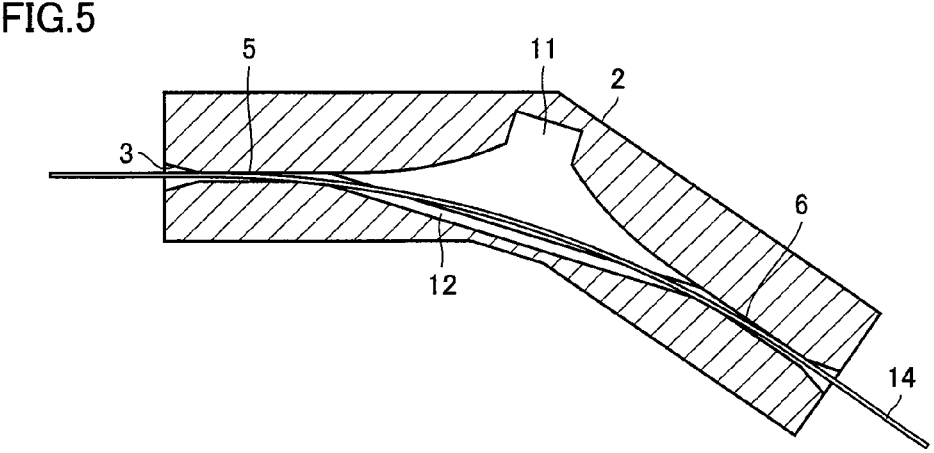
FIG. 5 is a cross-sectional schematic diagram showing such a state that a linear body passes through the measurement device.

An example in which the measurement device according to the present invention is applied to the wire for embolizing an aneurysm will now be described. FIG. 4 is a cross-sectional schematic diagram showing such a state that the sheath passes through the measurement device. FIG. 5 is a cross-sectional schematic diagram showing such a state that the linear body passes through the measurement device. In inserting the wire for embolizing an aneurysm into a human body via a catheter, an end portion of sheath 15 and an end portion of the catheter are connected to each other and delivery wire 14 is operated to move coil 13 into the catheter. Here, as shown in FIG. 2, a dimension of a cross-section of restraint portion 5, 6 perpendicular to a direction of extension thereof is formed to be equal to a dimension of a cross-section of groove 12. Therefore, as shown in FIG. 4, sheath 15 greater in diameter than delivery wire 14 can pass through measurement device main body 2 via restraint portion 6, groove 12 and restraint portion 5 within measurement device main body 2. When sheath 15 is pulled out from measurement device main body 2 after it is confirmed that coil 13 has completely moved into the catheter, only delivery wire 14 remains within measurement device main body 2 as shown in FIG. 5. As delivery wire 14 is smaller in diameter than sheath 15, it can move within space 11 in through hole 3. Therefore, in FIG. 5, delivery wire 14 is not located in groove 12 but bent in space 11.

Thus, in a location other than groove 12 in space 11, the height in a direction perpendicular to the sheet surface is slightly larger than the diameter of linear body 1 (that is, delivery wire 14) and an operation of linear body 1 in the direction perpendicular to the sheet surface is restrained. Accordingly, the height of the peak of bending of linear body 1 when compressive force in the direction of longitudinal axis is applied to linear body 1 can be set. Therefore, sheath 15 is permitted to pass through measurement device main body 2 without lowering accuracy in measurement of compressive force applied to linear body 1.

In addition, in FIG. 2, groove 12 is formed along inner wall 7 of through hole 3. Namely, when compressive force in the direction of longitudinal axis is applied to linear body 1 to bend linear body 1 in space 11, linear body 1 moves to the outside of bending and hence groove 12 is formed at a location irrelevant to movement of linear body 1 involved with bending. Therefore, lowering in accuracy in measurement of compressive force caused by interference of groove 12 with bending of linear body 1 can be prevented.

In an example where sheath 15 is permitted to pass through through hole 3 in the measurement device where groove 12 is not formed in through hole 3, as sheath 15 is greater in diameter than delivery wire 14, the operation of delivery wire 14 (linear body 1) in the direction perpendicular to the sheet surface cannot sufficiently be restrained in space 11. Therefore, when compressive force in the direction of longitudinal axis is applied to linear body 1, the height of the peak of bending of linear body 1 is not set and accuracy in measuring compressive force is lowered. In order to prevent this lowering in measurement accuracy, it has been necessary not to permit sheath 15 to pass through through hole 3. Namely, it has been necessary to adopt a method of connecting the end portion of sheath 15 and the end portion of the catheter to each other while the wire for embolizing an aneurysm with coil is not attached to measurement device main body 2, moving coil 13 into the catheter and thereafter connecting the catheter and measurement device main body 2 to each other, which has been inconvenient for use. In contrast, by using measurement device main body 2 in which groove 12 is formed in through hole 3, the wire with sheath 15 being attached thereto can be inserted in through hole 3 of the measurement device, and therefore, an easy-to-use measurement device can be provided.

Figure 6:
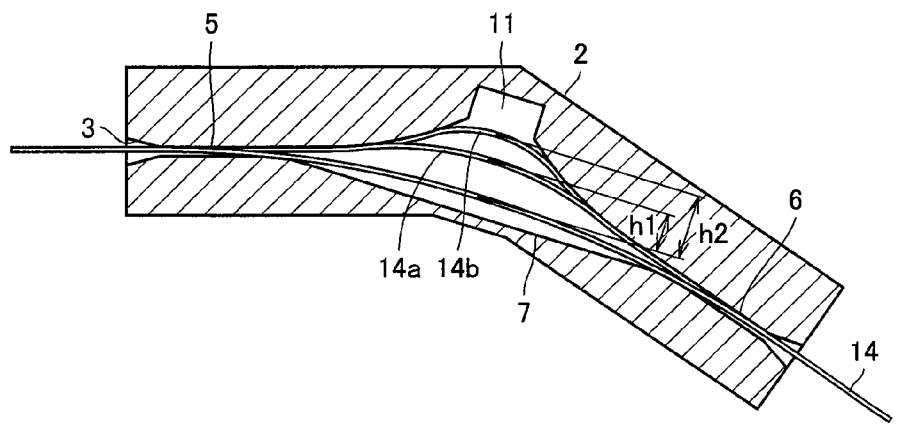
FIG. 6 is a cross-sectional schematic diagram showing such a state that compressive force is applied to the linear body.

A specific operation of the measurement device when compressive force in the direction of longitudinal axis is applied to the linear body will be described. FIG. 6 is a cross-sectional schematic diagram showing such a state that compressive force is applied to the linear body. In FIG. 6, when compressive force is applied to delivery wire 14 (linear body 1), delivery wire 14 is bent in space 11 of through hole 3 and the height of the peak of bending, that is, a distance from inner wall 7 to linear body 1, increases with increase in compressive force. For example, when compressive force p1 is applied, the delivery wire is bent as shown with a delivery wire 14a, and the height of the peak of bending increases by h1 as compared with a state where compressive force is not applied to delivery wire 14. Similarly, when compressive force p2 greater than p1 is applied, the delivery wire is bent as shown with a delivery wire 14b, and the height of the peak of bending increases by h2 as compared with a state where compressive force is not applied to delivery wire 14. Thus, the height of the peak of bending, that is, a degree of bending, is detected by using a sensor. By converting the degree of bending to compressive force applied to delivery wire 14 (linear body 1) based on predetermined correlation between the height of the peak of bending and compressive force applied to delivery wire 14 (linear body 1) by using a not-shown conversion circuit, compressive force can be measured.

Figure 7:
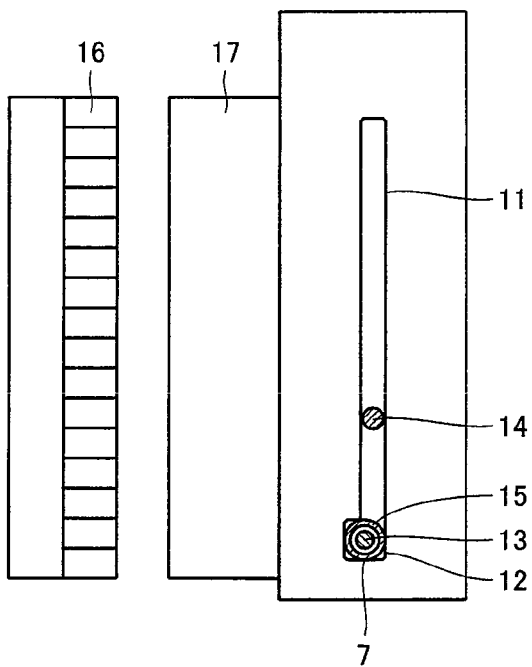
FIG. 7 is a cross-sectional schematic diagram showing an optical system detecting a degree of bending of the linear body when the linear body passes through the measurement device.

FIG. 7 is a cross-sectional schematic diagram showing an optical system detecting a degree of bending of the linear body when the linear body passes through the measurement device along the line VII-VII shown in FIG. 2. For example, a line sensor 16 (a one-dimensional optical array sensor, that has a plurality of light-receiving elements receiving light arranged in line) can be used as the sensor detecting the degree of bending. When line sensor 16 receives light emitted by a not-shown light source arranged at a position opposed to line sensor 16 across space 11, delivery wire 14 is located over a certain light-receiving element and delivery wire 14 cuts off light emitted by the light source. Then, a quantity of light received by that light-receiving element decreases. By detecting a position of that light-receiving element, a position of delivery wire 14 can be specified and the height of the peak of bending, that is, the degree of bending, of delivery wire 14 can be detected. In order to appropriately form an image of delivery wire 14 over line sensor 16, an optical element such as a lens, a slit, or a filter cutting off outside light may be provided in the present optical system. For example, in FIG. 7, a lens 17 such as Selfoc® lens is arranged between space 11 and line sensor 16.

As described above, when sheath 15 accommodating coil 13 passes through measurement device main body 2, groove 12 serves as a path. In FIG. 7, the width of groove 12 is shown in the vertical direction of the sheet and the depth of groove 12 is shown in the horizontal direction thereof. Namely, regarding groove 12, the dimension in a direction in which linear body 1 is bent within through hole 3 is the width of groove 12, and the dimension in a direction substantially orthogonal to the direction in which linear body 1 is bent within through hole 3 is the height of groove 12. Space 11 is formed such that inner wall 8, 9 is distant from inner wall 7 by a distance exceeding the sum of the width of groove 12 and the diameter of delivery wire 14 (linear body 1). Delivery wire 14 can move to the outer side of bending, that is, in the upward direction in FIG. 7, when compressive force in the direction of longitudinal axis is applied thereto. As the operation of delivery wire 14 in space 11 in the horizontal direction in FIG. 7 is restrained, the position of delivery wire 14 in space 11 when compressive force in the direction of longitudinal axis is applied to delivery wire 14 can be set. In addition, FIG. 7 shows such a state that sheath 15 cannot move to space 11 as its movement in a direction other than the direction of longitudinal axis is restricted by groove 12.

Figure 8:
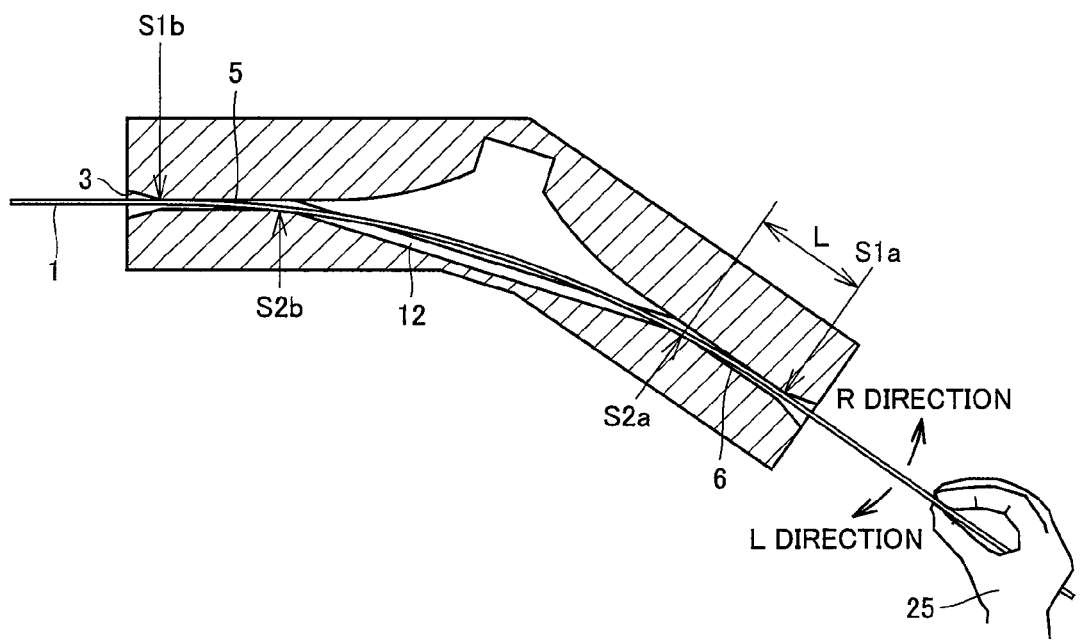
FIG. 8 is a cross-sectional schematic diagram showing such a state that force in an R direction or an L direction together with compressive force is applied to the linear body.

It is not always the case, however, that force is applied along the direction of longitudinal axis of linear body 1 when linear body 1 is operated. FIG. 8 is a cross-sectional schematic diagram showing such a state that force in an R direction or an L direction together with compressive force is applied to the linear body. In FIG. 8, it is possible that, when an operator 25 operates linear body 1, he/she applies force thereto, for example, while bending linear body 1 in the R direction or the L direction. In the measurement device in which groove 12 is formed along through hole 3 as shown in FIG. 2, the dimension of the cross-section of restraint portion 5, 6 perpendicular to the direction of extension thereof is formed to be equal to the dimension of the cross-section of groove 12. Here, even though linear body 1 is operated while it is bent in the direction perpendicular to the sheet surface when linear body 1 passes through through hole 3, influence is less because linear body 1 is restrained in space 11. On the other hand, when linear body 1 is operated while it is bent in the direction horizontal to the sheet surface such as the R direction or the L direction shown in FIG. 8, linear body 1 may be in point contact at four points (S1a, S2a, S1b, and S2b) at end portions in the direction of extension of restraint portion 5, 6 within through hole 3. Here, the degree of bending of linear body 1 when compressive force is applied to linear body 1 is not uniquely be set, which leads to lowering in measurement accuracy. Accordingly, the structure should be such that influence of the compressive force on measurement accuracy brought about by bending in the R direction or the L direction is minimized.

Figure 9:
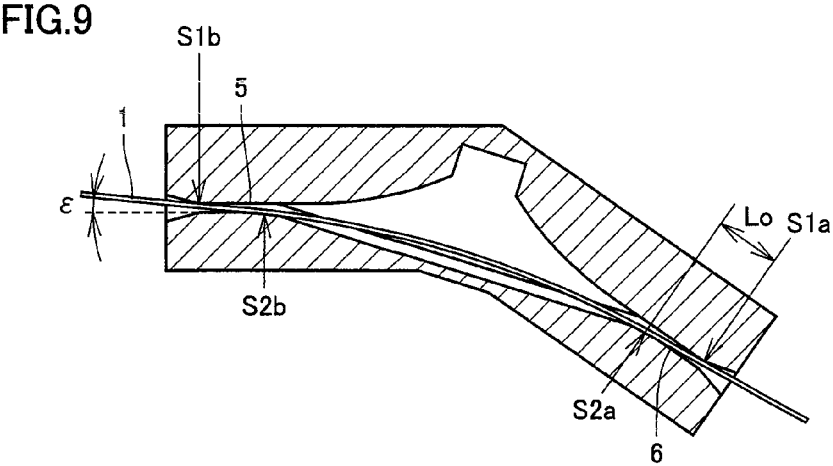
FIG. 9 is a cross-sectional schematic diagram showing the measurement device having a restraint portion short in length.
Figure 10:
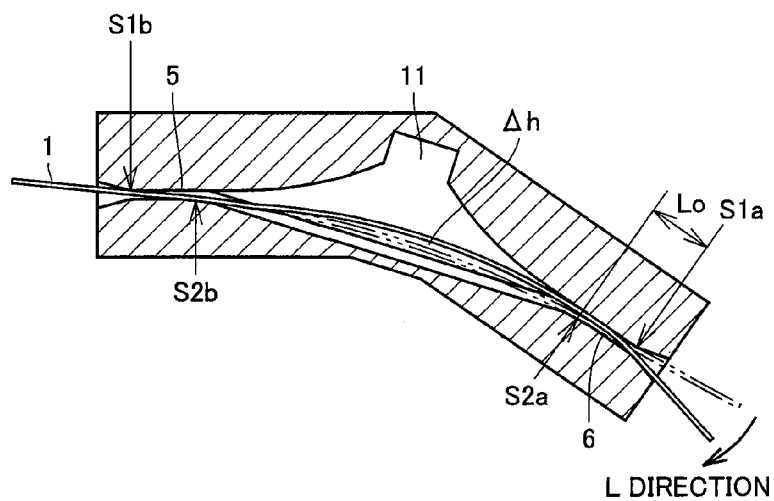
FIG. 10 is a cross-sectional schematic diagram showing an error factor in measurement of compressive force with the measurement device having the restraint portion short in length.

Specifically, in restraint portion 5, 6, it is necessary to set a length L of restraint portion 5, 6 in the direction of extension such that restraint portion 5, 6 is in parallel to linear body 1. FIG. 9 is a cross-sectional schematic diagram showing the measurement device having a restraint portion short in length. FIG. 10 is a cross-sectional schematic diagram showing an error factor in measurement of compressive force with the measurement device having the restraint portion short in length. In FIG. 9, restraint portion 5, 6 has an insufficient length Lo as the length in the direction of extension, and linear body 1 is in point contact at four points (S1a, S2a, S1b, and S2b) within through hole 3. Therefore, restraint portion 5, 6 is not in parallel to linear body 1, but an angle $\epsilon$ is formed therebetween. Here, when force is applied to linear body 1 in the L direction to bend linear body 1 as shown in FIG. 10, linear body 1 is bent in space 11 as a result of movement of linear body 1 in the L direction outside measurement device main body 2 and the position of linear body 1 is displaced by $\Delta h$ in a central portion of space 11. Therefore, error in connection with the height of the peak of bending of linear body 1 becomes significant and accuracy in measurement of compressive force is lowered.

Here, through hole 3 is formed such that the restraint portion has a such a length L that linear body 1 is in parallel to restraint portion 5, 6 outside the port of measurement device main body 2 through which linear body 1 passes, when linear body 1 passes through through hole 3 and external force other than gravity is not applied to the linear body. In order to measure parallelism between linear body 1 and restraint portion 5, 6, a ruler is placed along the centerline of through hole 3 in restraint portion 5, 6, to measure displacement of the ruler from linear body 1 at an appropriate position outside the port of measurement device main body 2. This displacement is a distance to linear body 1 in a direction of right angle with respect to the ruler. Using this displacement J and a distance K from the port of measurement device main body 2 to a measurement point, angle $\epsilon$ is calculated with an arctangent function. In other words, angle $\epsilon$ is calculated as $\epsilon=\arctan(J/K)$. Whether linear body 1 is in parallel to restraint portion 5, 6 is determined based on calculated angle $\epsilon$.

More specifically, for example, a linear body having a Young's modulus of 130 GPa, a diameter of 0.014 inch (0.356 mm) and a length of 180 cm is employed. Displacement J is then measured at distance K=10 cm from the port of measurement device main body 2 to the measurement point, to find angle $\epsilon$. If angle $\epsilon$ is 1° or smaller, it is determined that linear body 1 is in parallel to restraint portion 5, 6. Thus, the measurement device in which through hole 3 is formed such that linear body 1 is in parallel to restraint portion 5, 6 can be obtained. In an example where groove 12 is formed in the inner wall of through hole 3 to penetrate measurement device main body 2 along through hole 3 as well, lowering in accuracy in measurement of compressive force in the direction of longitudinal axis applied to linear body 1 can be prevented by defining the length of restraint portion 5, 6 based on parallelism between linear body 1 and restraint portion 5, 6.

Alternatively, in an example where it is not necessary to take into consideration use of the wire having the coil for embolizing an aneurysm attached at the tip end, it is not necessary to form a groove in the inner wall of through hole 3. Here, restraint portion 5, 6 can restrain the operation of linear body 1 in a direction other than the direction of longitudinal axis by making the diameter of through hole 3 in restraint portion 5, 6 slightly larger than the diameter of linear body 1 (for example, not smaller than 105% and not larger than 120% of the diameter of linear body 1) and making length L of restraint portion 5, 6 a few or more times greater than the diameter of linear body 1. Here, the minimum value of length L of restraint portion 5, 6 to achieve angle $\epsilon$ not larger than 1° is determined with the method above, and the measurement device in which through hole 3 is formed to have thus determined length L is achieved. Thus, a smaller size of the measurement device can be achieved without lowering accuracy in measurement of compressive force.

Figure 11:
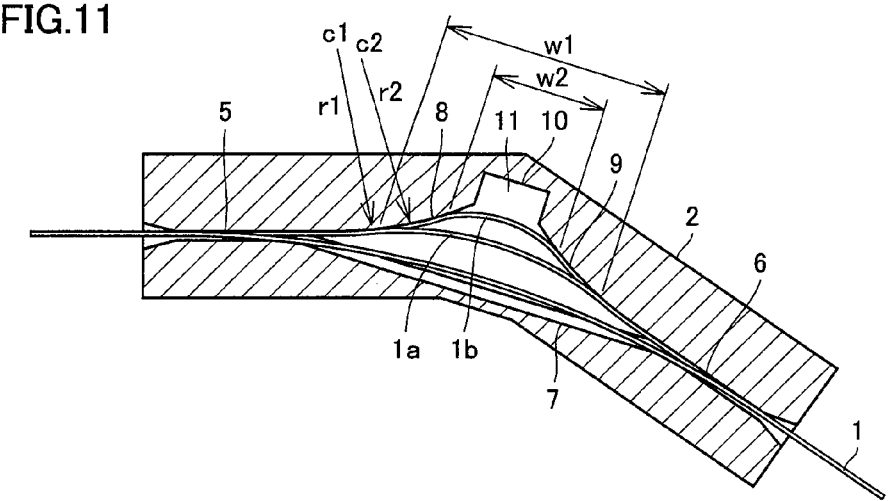
FIG. 11 is a cross-sectional schematic diagram showing such a state that compressive force is applied to different types of linear bodies.
Figure 12:
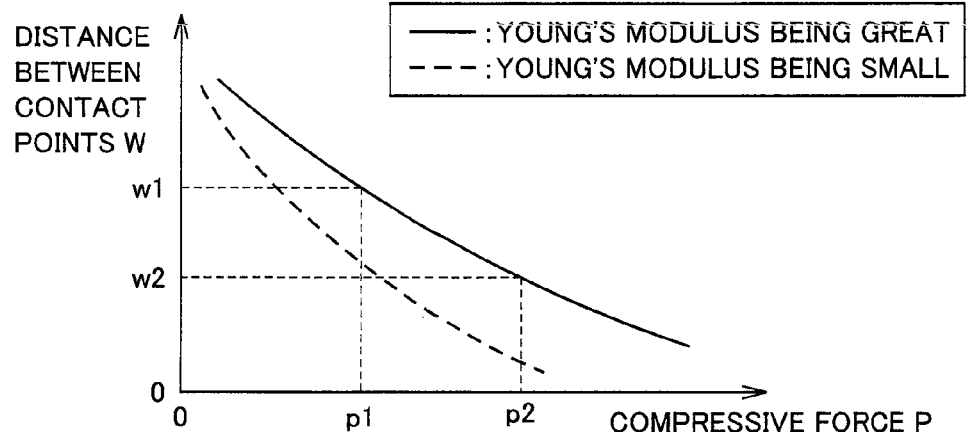
FIG. 12 is a graph showing relation between compressive force applied to the linear body and a distance between contact points.

An optimal shape of the through hole when the same measurement device is applied to linear bodies of various materials will now be described. FIG. 11 is a cross-sectional schematic diagram showing such a state that compressive force is applied to different types of linear bodies. FIG. 12 is a graph showing relation between compressive force applied to the linear body and a distance between contact points. Here, the contact point refers to a point at which linear body 1 moves away from inner wall 8 and inner wall 9 of through hole 3 when compressive force in the direction of longitudinal axis is applied to linear body 1 to bend linear body 1. Namely, a distance W between contact points indicates a distance between a point where linear body 1 is in contact with inner wall 8 and a point where linear body 1 is in contact with inner wall 9.

Linear bodies 1 of different type that have substantially the same diameter can be inserted in the same measurement device. Here, linear bodies 1 of different type may be different in the Young's modulus. If the Young's modulus is different among the linear bodies of different type, deflection under the same compressive force is different. Namely, as linear body 1 that has a small Young's modulus and is great in deflection tends to buckle, distance W between the contact points should be made smaller to avoid buckling. On the other hand, in linear body 1 that has a large Young's modulus and is small in deflection, distance W between the contact points should be made larger in order to measure compressive force with sufficient accuracy.

Here, through hole 3 is formed such that inner wall 8 and inner wall 9 in space 11 is in a shape of a curved surface convex toward the inside of through hole 3. In FIG. 11, a curved surface portion of inner wall 8 having a radius of curvature r1 and a center of radius of curvature at c1 is formed tangent to the inner wall of through hole 3 in restraint portion 5. In addition, a curved surface shape having a radius of curvature r2 and a center of radius of curvature at c2 is formed tangent to the curved surface portion having radius of curvature r1 above. The shape of inner wall 8 and inner wall 9 is not limited as above, and such a curved surface shape as convex toward the inside of through hole 3 and tangent to the inner wall of through hole 3 in restraint portion 5 should only be set.

Here, an example where equal compressive force is applied to two types of linear bodies different in the Young's modulus is considered. In FIG. 12, when the Young's modulus is great, relation between compressive force P and distance W between the contact points as shown with a solid line in FIG. 12 is obtained, and for example, distance W between the contact points when compressive force p1 is applied is w1. Alternatively, when the Young's modulus is small, relation as shown with a dashed line in FIG. 12 is obtained; distance W between the contact points when the same compressive force p1 is applied is smaller and the degree of bending of the linear body is greater. Here, as the linear body is bent in space 11 along inner wall 8 and inner wall 9 of through hole 3 on the outer side of bending of linear body 1, buckling of linear body 1 within space 11 can be prevented. Namely, as the linear body is bent in space 11 without buckling when compressive force in the direction of longitudinal axis is applied to the linear body having a small Young's modulus, the degree of bending of the linear body can be detected. By converting the detected degree of bending into compressive force in the direction of longitudinal axis applied to the linear body, compressive force applied to the linear body can be measured. Thus, compressive force in the direction of longitudinal axis applied to the linear body can accurately be measured with the same measurement device over a wide range, regardless of magnitude of the Young's modulus.

In addition, in FIG. 11, a recess 10 is formed between inner wall 8 and inner wall 9 in space 11. Compressive force in a wider range can thus accurately be measured. Specifically, as compressive force applied to linear body 1 can be measured by detecting the height of the peak of bending of linear body 1 in space 11, compressive force applied to linear body 1 can be measured unless a vertex of the peak of bending of linear body 1 within space 11, that is, a point most distant from inner wall 7 in linear body 1 located within space 11, comes in contact with the inner wall of space 11. As recess 10 is formed, in order to bring the vertex of the peak of bending of linear body 1 in contact with the inner wall in space 11, greater compressive force in the direction of longitudinal axis should be applied. Therefore, a range of measurement of compressive force can be broadened.

In addition, space 11 is formed in such a shape that inner wall 8, 9 forming a curved surface shape convex toward the inside of through hole 3 and recess 10 are combined. As a result of this shape of space 11, when compressive force is applied to linear body 1 to bend linear body 1 in space 11, a part of linear body 1 (a part corresponding to distance w1 or w2 between the contact points in FIG. 11) is distant from the inner wall (inner wall 8 and inner wall 9) of through hole 3 located on the outer side of bending of linear body 1. As compressive force increases, the distance between the contact points at which linear body 1 moves away from the inner wall decreases. In other words, relation between compressive force P and distance W between the contact points is as shown in the graph in FIG. 12. For example, when compressive force p1 is applied to the linear body having relation between compressive force P and distance W between the contact points shown with the solid line in FIG. 12, the linear body is bent as shown with a linear body 1a and the distance between the contact points at that time attains to w1. Alternatively, when compressive force p2 greater than p1 is applied to the linear body, the linear body is bent as shown with a linear body 1b and the distance between the contact points at that time attains to w2 smaller than w1.

As a result of such a structure of space 11, when compressive force in the direction of longitudinal axis is applied to linear body 1 to bend linear body 1 in space 11 within through hole 3 in which linear body 1 is bent, linear body 1 can be bent along the inner wall (inner wall 8 and inner wall 9) of through hole 3 located on the outer side of bending of linear body 1. In addition, a part of linear body 1 can be bent away from inner wall 8 and inner wall 9. Moreover, as compressive force increases, the distance between the contact points at which linear body 1 moves away from the inner wall decreases. Therefore, as buckling of linear body 1 within space 11 can be prevented, the degree of bending of the linear body can accurately be detected without buckling of a linear body of which buckling load is small. By converting the detected degree of bending into compressive force in the direction of longitudinal axis applied to the linear body, compressive force applied to the linear body can be measured. Correlation between compressive force and the degree of bending is determined in advance with regard to various linear bodies different in the Young's modulus and such correlation is stored in the conversion circuit, so that correlation is selected in accordance with a linear body to be used. Thus, a measurement device capable of measuring compressive force in the direction of longitudinal axis applied to linear body 1 regardless of magnitude of buckling load of linear body 1 can be provided, and the same measurement device is applicable to linear bodies 1 of various materials, which leads to cost efficiency.

Figure 13:
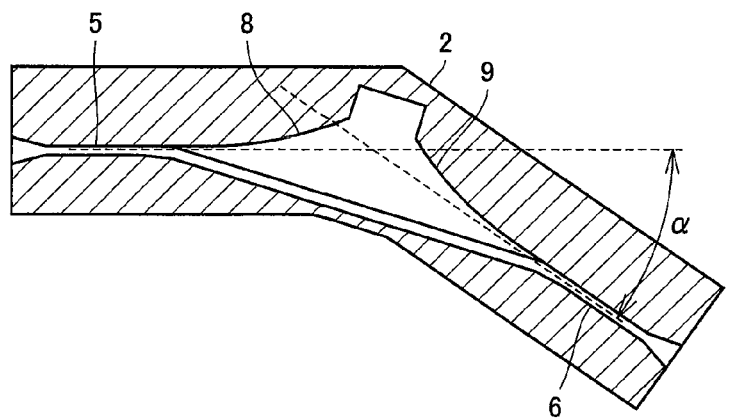
FIG. 13 is a cross-sectional schematic diagram showing an appropriate angle formed by the restraint portions of the through hole.
Figure 14:
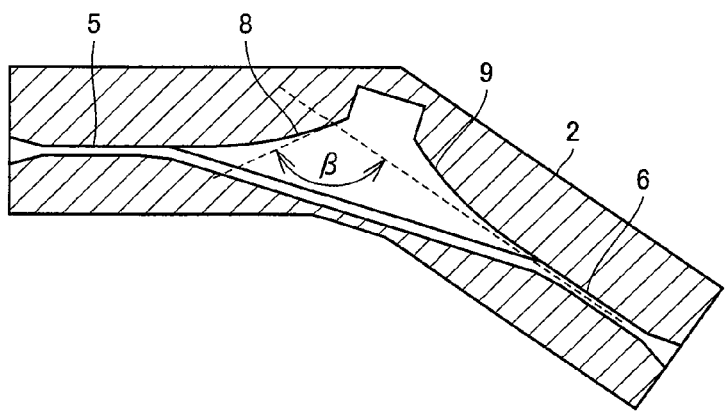
FIG. 14 is a cross-sectional schematic diagram showing an appropriate angle formed by the restraint portion of the through hole and an inner wall.

In addition, the shape of through hole 3 is defined such that linear body 1 can readily pass through measurement device main body 2 when it is inserted in measurement device main body 2. FIG. 13 is a cross-sectional schematic diagram showing an appropriate angle formed by the restraint portions of the through hole. FIG. 14 is a cross-sectional schematic diagram showing an appropriate angle formed by the restraint portion of the through hole and the inner wall. In FIG. 13, through hole 3 is formed to have restraint portions 5, 6 restricting movement of linear body 1 in a direction other than the direction of longitudinal axis at its opposing end portions, and an angle between the extension of restraint portion 5 (that is, the extension of the centerline of restraint portion 5) and the extension of restraint portion 6 (that is, the extension of the centerline of restraint portion 6) shown with dashed lines in FIG. 13 is denoted as α. In addition, an angle between the extension of restraint portion 6 and the tangent to the inner wall of through hole 3 located on the outer side of bending of linear body 1, that is, inner wall 8, at a point on the extension of restraint portion 6 shown with dashed lines in FIG. 14 is denoted as β. A range of angle α, β and reasons therefor will be described hereinafter.

$$\alpha+\beta\leq160° \quad\quad (A)$$

Relation of α+β=180° indicates such a state that the inner wall such as inner wall 8 of through hole 3 located on the outer side of bending of linear body 1 is located on the extension of restraint portion 5. Here, as there is no space on the outer side of bending of linear body 1, displacement of linear body 1 when compressive force in the direction of longitudinal axis is applied to linear body 1 is substantially zero. Therefore, as the degree of bending of linear body 1 corresponding to compressive force cannot be detected, the measurement device is of no use. Therefore, making allowance of 20°, relation of α+β≤160° is defined.

$$\beta\geq100 \quad\quad (B)$$

The linear body having a Young's modulus of 130 GPa and a diameter of 0.014 inch (0.356 mm) was used to experimentally set a range of β. Here, β=90° indicates such a state that linear body 1 is in contact at right angle with the inner wall of through hole 3 located on the outer side of bending of linear body 1. If β is 90° or smaller, it is impossible to guide linear body 1 into through hole 3. Accordingly, in consideration of friction between the linear body and the inner wall, relation of $\beta \geq 100°$ is defined. Preferably, by setting relation of $\beta \geq 110°$, linear body 1 can more readily pass through through hole 3.

$$30° \leq \alpha \leq 50° \quad (C)$$

The linear body having a Young's modulus of 130 GPa and a diameter of 0.014 inch (0.356 mm) and the linear body having a Young's modulus of 90 GPa and a diameter of 0.012 inch (0.305 mm) were used to experimentally set a range of $\alpha$. When $\alpha$ is made greater, friction force at the point where linear body 1 comes in contact with the inner wall of through hole 3 located on the outer side of bending of linear body 1 is not ignorable and accuracy in measuring compressive force lowers. On the other hand, when $\alpha$ is made smaller, the degree of bending when compressive force is applied to linear body 1 becomes smaller and sensitivity of the measurement device to compressive force lowers. Therefore, relation of $30° \leq \alpha \leq 50°$ is defined. If $\alpha$ is 35° or smaller, reduction in friction force is small. On the other hand, when $\alpha$ is 45° or greater, increase in friction force is significant. Accordingly, relation of $35° \leq \alpha \leq 45°$ is preferably defined.

Based on the equations (A), (B) and (C) above, the following relation is derived.

$$30° \leq \alpha \leq 50°$$

$$100° \leq \beta \leq 130°$$

Therefore, angle $\alpha$ between the extension of restraint portion 5 and the extension of restraint portion 6 is defined and angle $\beta$ between the extension of restraint portion 6 and the tangent to the inner wall of through hole 3 located on the outer side of bending of linear body, that is, inner wall 8, at the point on the extension of restraint portion 6 is defined, so that the linear body can readily pass through the measurement device main body when it is inserted in the measurement device main body.

Figure 15:
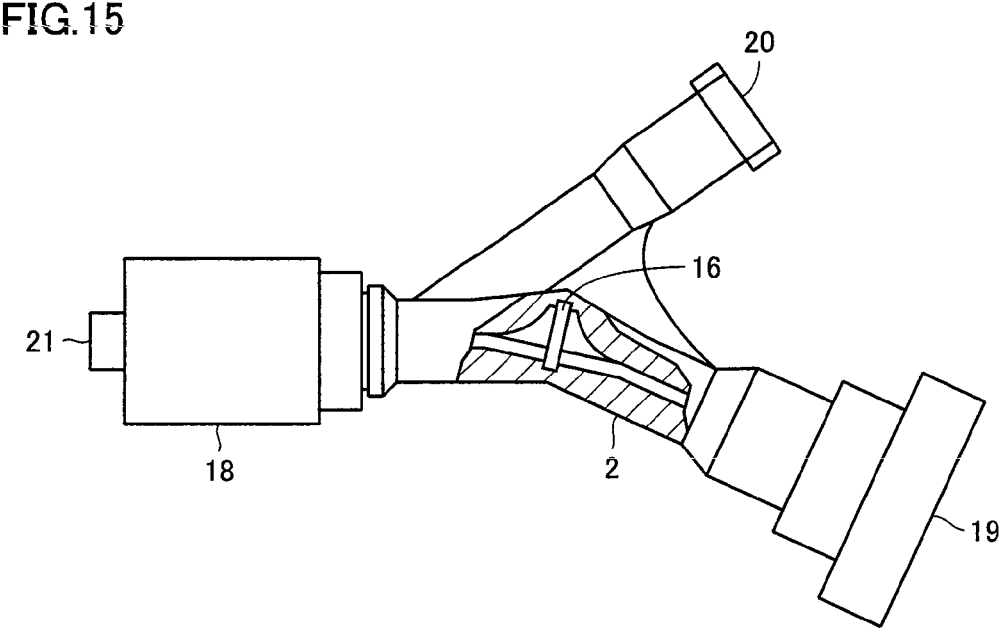
FIG. 15 is a schematic diagram showing an example of incorporation for use in a Y-connector.

Incorporation for use in other medical equipment, of the measurement device measuring compressive force in the direction of longitudinal axis applied to the linear body representing a linear medical appliance to be inserted in a vessel in a body is shown as an example of practical use of the measurement device according to the present invention. FIG. 15 is a schematic diagram showing an example where the measurement device main body is incorporated for use in a Y-connector. In FIG. 15, a Y-connector 18 includes an input port 19, another input port 20, and an output port 21. Measurement device main body 2 is incorporated in a passage communicating between input port 19 and output port 21 within Y-connector 18. Linear body 1 is a linear medical appliance such as a guide wire or a catheter inserted in a vessel in a body such as a blood vessel and a ureter, or a wire having a coil attached at a tip end for embolizing an aneurysm, and it is guided to a destination in the body through an operation from the input port 19 side.

By thus measuring increase in compressive force in the direction of longitudinal axis applied to the linear medical appliance inserted in the vessel in the body, load applied to the vessel in the body by the medical appliance can be measured as reaction force against compressive force. Namely, contact of the tip end of the medical appliance with the inner wall of the vessel can be sensed. Therefore, application of excessive load onto the vessel in the body can be prevented. In addition, as the measurement device according to the present invention is incorporated in Y-connector 18, the linear medical appliance is operated through input port 19 of Y-connector 18 while a medicine can be injected through another input port 20. For example, physiological saline for reducing friction between the catheter and the guide wire can be injected through another input port 20. In addition, for example, after the catheter inserted in the blood vessel is guided from the outside of a human body to the destination, a contrast medium can be injected through another input port 20 so that the contrast medium can reach the destination in the body.

Figure 16:
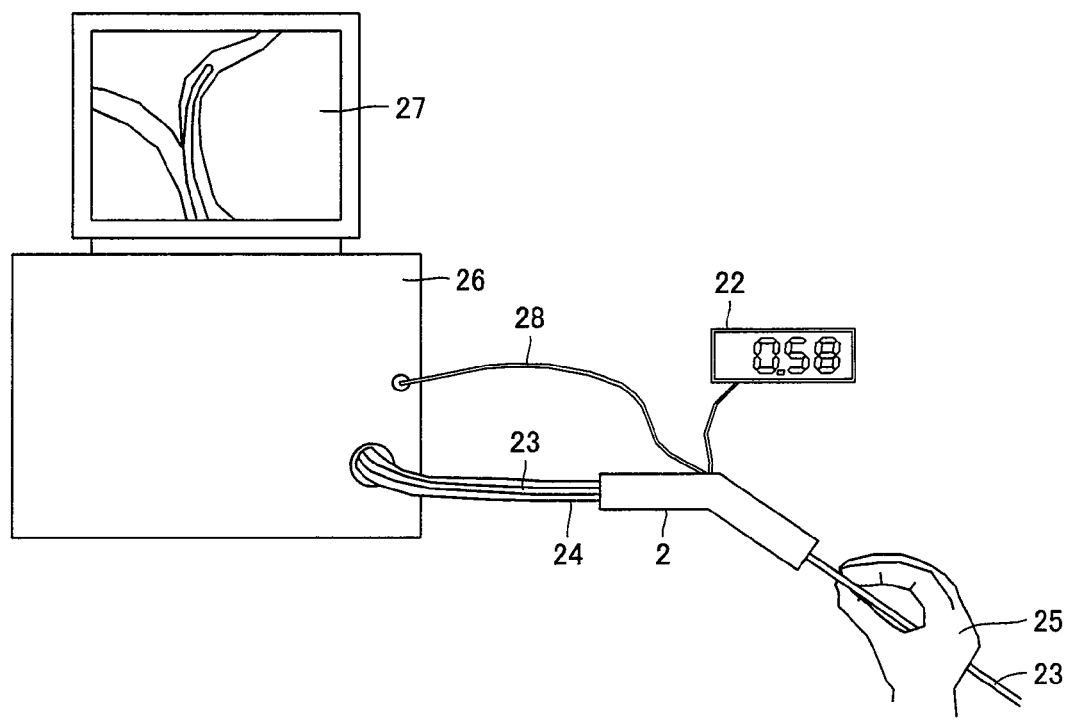
FIG. 16 is a schematic diagram showing an example where the measurement device is attached to a training simulator simulating a human body for use.

FIG. 16 is a schematic diagram showing an example where the measurement device is attached to a training simulator simulating a human body for use. In FIG. 16, a simulator 26 displays a simulated perspective image 27 equivalent to a perspective image of a vessel in a human body in which a linear medical appliance is inserted. A catheter 24 is connected to measurement device main body 2, and a guide wire 23 passing through through hole 3 in measurement device main body 2 is located in catheter 24. Operator 25 in training operates guide wire 23 while viewing simulated perspective image 27. Simulator 26 varies the insertion resistance of inserted guide wire 23. If there is insertion resistance when operator 25 holding guide wire 23 applies force in the direction of longitudinal axis to guide wire 23, compressive force is applied to guide wire 23 in the direction of longitudinal axis. Resistance during operation, i.e., compressive force applied to guide wire 23 that is measured by the measurement device, is displayed on a visualizing instrument 22 and also transmitted to simulator 26 through a cable 28, thus contributing to change in the insertion resistance of guide wire 23 in simulator 26. Though measurement device main body 2 is separate from simulator 26 in FIG. 16, measurement device main body 2 may integrally be incorporated in simulator 26. Alternatively, instead of including visualizing instrument 22, compressive force applied to guide wire 23 may be displayed in simulated perspective image 27 of simulator 26.

Thus, manipulation of the skilled operator can be quantified and manipulation can quantitatively be transferred to the less experienced operator. Therefore, manipulation of the less experienced operator can quickly be improved.

In the description above, the line sensor has been given as an example of a sensor detecting a degree of bending of the linear body. Instead of the one-dimensional array sensor such as the line sensor, however, a two-dimensional array sensor, for example, implemented by arranging a plurality of light-receiving elements on a plane in matrix may be used to detect the degree of bending of the linear body. Further, as the degree of bending of the linear body should only be detected, for example, a non-contact distance sensor detecting the height of the peak of bending, a position sensor detecting a position of the linear body, or the like may also be employed.

It should be understood that the embodiments disclosed herein are illustrative and non-restrictive in every respect. The scope of the present invention is defined by the terms of the claims, rather than the description above, and is intended to include any modifications within the scope and meaning equivalent to the terms of the claims.

INDUSTRIAL APPLICABILITY

The measurement device according to the present invention is particularly advantageously applicable as a device for measuring compressive force applied to a linear body having flexibility, such as a linear medical appliance to be inserted in a vessel in a body.

The invention claimed is:

1. A measurement device measuring compressive force applied to a linear body having flexibility in a direction of longitudinal axis, comprising:
   a main body including a through hole through which said linear body passes, wherein said main body includes a fixed curved portion having an inner space to allow bending of said linear body disposed therein and said linear body is bent in a direction within said through hole inside said fixed curved portion of said main body when said compressive force is applied to said linear body;
a sensor for detecting a degree of bending;
a conversion circuit for converting detected said degree of bending into said compressive force applied to said linear body, based on predetermined correlation between said degree of bending and compressive force; and
a groove is disposed within said main body in an inner wall of said through hole along said through hole.

2. The measurement device according to claim 1, wherein
said groove is formed along said inner wall of said through hole located on an inner side of bending of said linear body within said through hole in which said linear body is bent, and
said through hole is disposed such that the distance between said inner wall of said through hole located on an outer side of bending of said linear body and said inner wall of said through hole located on the inner side of bending of said linear body is greater than a sum of a width of said groove and a diameter of said linear body to form said inner space within the fixed curved portion of said main body in which said linear body is bent.

3. The measurement device according to claim 1, incorporated in medical equipment for use.

4. The measurement device according to claim 1, attached to a training simulator simulating a human body for use.

5. A measurement device measuring compressive force applied to a linear body having flexibility in a direction of longitudinal axis, comprising:
a main body including a through hole through which said linear body passes, wherein said main body includes a fixed curved portion having an inner space to allow bending of said linear body disposed therein and said linear body is bent in a direction within said through hole inside said fixed curved portion of said main body when said compressive force is applied to said linear body;
a sensor for detecting a degree of bending;
a conversion circuit for converting detected said degree of bending into said compressive force applied to said linear body based on predetermined correlation between said degree of bending and compressive force, wherein:
said through hole includes restraint portions restricting movement of said linear body in a direction other than said direction of longitudinal axis, at opposing end portions of said through hole, and
said linear body is in parallel to said restraint portions outside a port of said main body through which said linear body passes, when said linear body passes through said through hole and no external force other than gravity is applied to said linear body.

6. The measurement device according to claim 5, further comprising a groove disposed within said main body in an inner wall of said through hole along said through hole.

7. A measurement device measuring compressive force in a direction of longitudinal axis applied to a linear body having flexibility, comprising:
a main body including a through hole through which said linear body passes, wherein said main body includes a fixed curved portion having an inner space to allow bending of said linear body disposed therein and said linear body is bent in a direction within said through hole inside said fixed curved portion of said main body when said compressive force is applied to said linear body;
a sensor for detecting a degree of bending;
a conversion circuit for converting detected said degree of bending into said compressive force applied to said linear body based on predetermined correlation between said degree of bending and compressive force, wherein:
said through hole is disposed such that an inner wall of said through hole located on an outer side of bending of said linear body is distant from said inner wall of said through hole located on an inner side of bending of said linear body to form an inner space within said fixed curved portion of said main body in which said linear body is bent, and
said through hole being formed such that said inner wall of said through hole located on the outer side of bending of said linear body is in a shape of a curved surface convex toward inside of said through hole.

8. The measurement device according to claim 7, wherein
said through hole is formed such that a part of said linear body is distant from said inner wall of said through hole located on the outer side of bending of said linear body when said compressive force is applied to said linear body to bend said linear body, and
said through hole is formed such that a distance (W) between contact points at which said linear body moves away from said inner wall is smaller as said compressive force increases.

9. The measurement device according to claim 7, wherein
said through hole includes restraint portions restricting movement of said linear body in a direction other than said direction of longitudinal axis, at opposing end portions of said through hole, and
said through hole is disposed such that an angle ($\alpha$) between extensions of said restraint portions is not smaller than 30° and not greater than 50°.

10. The measurement device according to claim 7, wherein
said through hole includes restraint portions restricting movement of said linear body in a direction other than said direction of longitudinal axis, at opposing end portions of said through hole, and
said through hole is disposed such that an angle ($\beta$) between an extension of said restraint portion and a tangent to said inner wall on the extension, of said through hole located on the outer side of bending of said linear body is not smaller than 100° and not greater than 130°.

* * * * *